United States Patent [19]

Chibata et al.

[11] 3,953,291

[45] Apr. 27, 1976

[54] PROCESS FOR PREPARING 6-AMINOPENICILLANIC ACID

[75] Inventors: Ichiro Chibata, Suita; Tetsuya Tosa, Kyoto; Tadashi Sato, Takatsuki, all of Japan

[73] Assignee: Tanabe Seiyaku Co., Ltd., Osaka, Japan

[22] Filed: Mar. 13, 1974

[21] Appl. No.: 450,655

[30] Foreign Application Priority Data
Mar. 24, 1973 Japan.................................. 48-33769

[52] U.S. Cl. ................................ 196/36 P; 195/54; 195/29; 195/30
[51] Int. Cl.²........................................... C12D 9/00
[58] Field of Search ....................... 195/54, 59, 36 P

[56] References Cited
UNITED STATES PATENTS

| | | | |
|---|---|---|---|
| 3,619,371 | 11/1971 | Crook et al. | 195/36 P |
| 3,736,230 | 5/1973 | Delin et al. | 195/36 P |
| 3,767,790 | 10/1973 | Guttag | 195/54 |
| 3,791,926 | 2/1974 | Chibata et al. | 195/59 |

*Primary Examiner*—Alvin E. Tanenholtz
*Attorney, Agent, or Firm*—Bierman & Bierman

[57] ABSTRACT

At least one acryloyl monomer is polymerized in an aqueous suspension containing a penicillin amidase-producing microorganism. The acryloyl monomers employed in the present invention include acryloylamide, N,N'-lower alkylene-bis-acryloylamide, bis(acryloylamidomethyl)ether and N,N'-diacryloylethyleneurea. The resultant immobilized penicillin amidase-producing microorganism is subjected to enzymatic reaction with penicillin. 6-Aminopenicillanic acid is produced.

14 Claims, No Drawings

PROCESS FOR PREPARING 6-AMINOPENICILLANIC ACID

This invention relates to a process for preparing 6-aminopenicillanic acid. More particularly, it relates to the production of 6-aminopenicillanic acid (hereinafter referred to simply as "6-APA") by enzymatic reaction of an immobilized penicillin amidase-producing microorganism with penicillin.

It is known in the art that 6-APA is prepared by enzymatic deacylation of penicillin, i.e., by the reaction of penicillin with penicillin amidase or a penicillin amidase-producing microorganism. However, this method is disadvantageous for a large scale production. 6-APA produced according to this method is contaminated with the enzyme, microbial cells, nutrient sources and/or proteins. Accordingly, additional steps of removing the enzyme, microbial cells and/or other contaminants from the product are required to recover 6-APA in high purity. Moreover, when the enzymatic reaction is completed, the reaction solution is boiled and/or acidified to destroy the enzyme or microorganism, and precipitates of the enzyme or microorganism are filtered off. Thus, penicillin amidase or the penicillin amidase-producing microorganism can be used only once and must be discarded thereafter. Alternatively, it is known that 6-APA is prepared by chemical deacrylation of penicillin. For example, penicillin is reacted with triphenylmethyl chloride to give triphenylmethyl ester of penicillin. Said ester is treated with phosphorus trichloride. Then, the triphenylmethyl ester of $N^{imino}$-chloropenicillin thus obtained is reacted with methanol to give the corresponding $N^{imino}$-methoxy-penicillin ester. 6-APA is obtained by hydrolyzing said $N^{imino}$-methoxy-penicillin ester with aqueous ammonia. In the commercial production of 6-APA, however, this chemical method is also disadvantageous because of lengthy procedures involved therein and/or low yield of 6-APA to be obtained.

One object of the present invention is to provide a novel immobilized microorganism which affords high activity of penicillin amidase for a long period of time. Another object of the invention is to provide an immobilized penicillin amidase-producing microorganism which obviates the necessity of discarding the microorganism and allows its reuse in successive operations. Another object of the invention is to provide an improved method of preparing 6-APA from penicillin by the use of a penicillin amidase-producing microorganism. A further object of the invention is to provide a method which eliminates the necessity of additional steps in separating the desired product, i.e., 6-APA, from the substances present in the reaction mixture. Still further objects of the present invention will be apparent from the descriptions which follow.

According to the present invention, 6-APA can be prepared by the steps of polymerizing at least one acryloyl monomer in an aqueous suspension of a penicillin amidase-producing microorganism, and subjecting the resultant immobilized penicillin amidase-producing microorganism to enzymatic reaction with penicillin.

Preferred examples of the penicillin amidase-producing microorganisms which are employed in the present invention include *Escheichia coli* ATCC 9637, *Escherichia coli* ATCC 11105, *Streptomyces griseus* IFO (Institute for Fermentation, Osaka, Japan) 3355, *Nocardia gardneri* ATCC 9604, *Micrococcus roseus* IFO 3764, *Pseudomonas aeruginosa* OUT (Faculty of Technology, Osaka University, Japan) 8252 and *Alkaligenes faecalis* OUT 8025. All of these microorganisms are publicly available from the above-mentioned depositories. In this connection, however, it shoud be noted that the present invention is not limited to the use of these specific microorganisms, but includes within its scope the use of all of penicillin amidase-producing microorganisms such as those belonging to the genera of Escherichia, Streptomyces, Nocardia, Alkaligenes, Micrococcus and Pseudomonas. Suitable amount of the penicillin amidase-producing microorganism which is employed in the present invention is 0.32 to 3.2 g, especially 0.95 to 1.9 g, per g of the acryloyl monomer or monomers used. The polymerization reaction of the present invention serves to tightly entrap each of the microorganisms into the lattice of the polymer thereby affording high enzymatic activity for a long period of time.

The polymerization reaction of the present invention can be carried out in the presence of a polymerizaton initiator and a polymerization accelerator. Potassium persulfate, ammonium persulfate vitamin $B_2$ and Methylene Blue are suitable as polymerization initiators. On the other hand, $\beta$-(dimethylamino)-propionitrile and N,N,N',N'-tetramethylethylenediamine are employed as polymerizaton accelerators. Suitable amount of polymerization initiator to be added to the aqueous suspension of the penicillin amidase-producing microorganism are 5 to 50 mg per g of the acryloyl monomer or monomers. Suitable amounts of polymerization accelerator to be added are 1.5 to 15 mg per g of the acryloyl monomer or monomers. It is preferred to carry out the reaction of 0° to 50°C, especially 20° to 40°C. The reaction may be completed within 10 to 60 minutes. The acryloyl monomers which are suitable for use in the present invention include acryloylamide, N,N'-lower alkylene-bis-acryloylamide, bis(acryloylamidomethyl)ether and N,N'-di-acryloyl-ethylene-urea(N,N'-acryloyl-imidazolidine-2-one). For the purpose of the present invention, it is suitable to entrap the penicillin amidase-producing microorganism with a polymer obtained from one or two monomers mentioned above, particularly with a copolymer of acryloylamide and an acryloyl monomer selected from the group consisting of N,N'-lower alkylene-bis-acryloylamide, bis(acryloylamidomethyl)ether and N,N'-di-acryloyl-ethyleneurea. N,N'-methylene-bis-acryloylamide and N,N'-propylene-bis-acryloylamide are preferably employed as the N,N'-lower alkylene-bis-acryloylamide. A suitable amount of N,N'-lower alkylene-bis-acryloylamide, bis(acryloylamidemethyl)ether or N,N'-acryloyl-ethylene-urea which is used to copolymerize with acryloylamide is 5 to 160 mg, especially 15 to 130 mg, more specifically 25 to 80 mg, per g of acryloylamide. After the polymerization reaction is completed as above, the resultant immobilized penicillin amidase-producing microorganism is granulated by passing it through a sieve to form particles of 2.5 to 5.5 mm, especially 3 to 4 mm in diameter.

6-APA can be prepared by enzymatic reaction of the immobilized penicillin amidase-producing microorganism with penicillin. The enzymatic reaction is carried out at 25° to 50°C, especially at 30° to 45°C. It is preferred to carry out reaction at a pH of 7 to 9.5, especially at pH 8 to 9. Any known penicillins can be used as a substrate of the present invention. Representative examples of said penicillins are shown by the following formula:

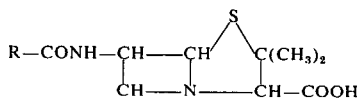

wherein R is an alkyl, alkenyl or aryl-alkyl group, or a group of the formula: $R^1-X-CH_2-$, $R^1$ is alkyl, alkenyl or aryl, and X is oxygen or sulfur. More specifically, for example, the known penicillins which are employed in the present invention include Penicillin G(benzylpenicillin), Penicillin K(n-heptylpenicillin), Penicillin X(p-hydroxybenzylpenicillin), Penicillin F(2-pentenylpenicillin), Dihydropenicillin F(n-amylpenicillin), Penicillin AT(allylmercaptomethylpenicillin), Penicillin BT (butylthiomethylpenicillin), Penicillin S(γ-chlorocrotylmercaptomethylpenicillin) and Penicillin V(phenoxymethylpenicillin).

The amount of the substrate which is dissolved in an aqueous suspension of a penicillin amidase-producing microorganism is not critical in the present invention. For example, penicillin is dissolved in water at any concentration. The aforementioned immobilized microorganism is suspended in the aqueous penicillin solution, and the suspension is stirred. After the reaction is completed, the mixture is filtered or centrifuged to recover the immobilized microorganism for subsequent use. 6-APA is recovered from the filtrate or supernatant solution. The optimum condition for complete conversion of penicillin to 6-APA can be readily obtained by adjusting the reaction time. Alternatively, the enzymatic reaction of the invention can be performed by a column method. The column method enables the reaction to be carried out in a successive manner. For example, the immobilized microorganism is charged into a column, and an aqueous penicillin solution is passed through the column at a suitable flow rate. An aqueous solution containing 6-APA is obtained as the effluent. 6-APA is recovered by a known method per se such as, for example, adjusting the effluent to a pH of 4 to 5. In carrying out the enzymatic reaction, the conversion rate of penicillin to 6-APA mainly depends upon the enzymatic potency of the immobilized microorganism, the temperature or the reaction time. In case of the column method, however, the optimum reaction condition for complete conversion of penicillin to 6-APA can be readily obtained by adjusting the flow rate of the substrate solution.

In any case, the immobilized microorganism of the present invention retains a high level of the enzymatic activity during the reaction. Moreover, due to the sufficient durability of the enzymatic activity thereof, the immobilized microorganism of the present invention can be used repeatedly for the enzymatic reaction.

Practical and presently-preferred embodiments of the present invention are shown in the following Examples. In this specification, the terminology "lower alkylene" should be interpreted as referring to an alkylene group having 1 to 4 carbon atoms. In the following Examples, the penicillin amidase activity of a microorganism or immobilized microorganism was expressed in terms of "units", and one unit was defined as the activity of the microorganism or immobilized microorganism which hydrolyzes one mg of Penicillin G by the reaction of an aqueous suspension of said microorganism with said penicillin at pH 9.0 at 40°C for 1 hour. Furthermore, the amount of 6-APA in a solution was assayed in accordance with the method described in "Industrial and Engineering Chemistry", 18, 619(1946) and "Analytical Chemistry", 33, 648(1961). That is, a 6-APA solution was adjusted to pH 2.0 with 2N-hydrochloric acid and washed with methyl-isobutylketone to remove penicillin and other contaminants. The amount of 6-APA in the aqueous layer thus obtained was first assayed colorimetrically in accordance with the Iodine Absorption Method. Then, the aqueous layer was further treated with phenylacetyl chloride to convert 6-APA to Penicillin G. The amount of 6-APA in said aqueous solution was again calculated on the basis of the anti-microbial activity thereof which was assayed in accordance with the Paper Disc Method.

Example 1

1. An aqueous nutrient medium (pH 7.0) containing the following ingredients is prepared:

| Peptone | 2 w/v % |
|---|---|
| Monopotassium phosphate | 0.3 |
| Dipotassium phosphate | 0.7 |
| Yeast extract | 0.5 |
| Magnesium sulfate 7 H$_2$O | 0.02 |
| Ferric chloride 6 H$_2$O | 0.02 |
| Sodium L-glutamate | 0.5 |
| Phenoxyacetic acid | 0.2 |

*Escherichia coli* ATCC 9637 is inoculated into one liter of the medium. The medium is cultivated at 30°C for 24 hours under shaking. Then, the medium is centrifuged. The microbial cells thus collected show the penicillin amidase activity of 6.5 units/g. 12 g of the microbial cells are suspended in 48 ml of a physiological saline solution. 9 g of acryloylamide, 480 mg of N,N'-methylene-bis-acryloylamide, 6 ml of 5 % β-(dimethylamino)-propionitrile and 6 ml of 2.5 % potassium persulfate are added to the suspension. Then, the suspension is allowed to stand at 37°C for 30 minutes. After the reaction is completed, the suspension is filtered. The stiff gel obtained is granulated by passing it through a sieve to form particles of 3 mm in diameter. 120 ml of an immobilized preparation of *Escherichia coli* ATCC 9637 are obtained. Penicillin amidase activity: 4.7 units/ml.

2. 120 ml of the immobilized preparation of *Escherichia coli* ATCC 9637 are charged into a 2.1 cm × 34.8 cm column. 500 ml of an aqueous 1 % potassium Penicillin G solution (pH 9.0) are passed through the column at 40°C at the flow rate of 16 ml/hr. The effluent tus obtained is adjusted to pH 2.0 with 2N-hydrochloric acid and washed twice with 10 ml of methylisobutylketone to remove phenylacetic acid. The aqueous layer is again adjusted to pH 7.0 with 2N-sodium hydroxide. Then, the aqueous layer is concentrated at 50°C under reduced pressure to bring its total volume to 5 ml. After adjusting to pH 4.3 with 2N-hydrochloric acid, the concentrated solution is allowed to stand at 27°C overnight. The crystalline precipitate is collected by filtration and dried at 50°C under reduced pressure. 2.23 g of 6-APA are obtained. Yield: 85 % M.p. 204° – 207°C (decomp.)

Example 2

An immobilized preparation of *Escherichia coli* ATCC 9637 is prepared in the same manner as described in Example 1 — (1). 120 ml of the immobilized preparation are charged into a 2.1 cm × 34.8 cm column. An aqueous 1 % potassium Penicillin G solution (pH 9.0) is passed through the column at 40°C at a flow rate as shown in Table 1. The percentage conversion of Penicillin G to 6-APA in the effluent is shown in Table 1.

Table 1

| Flow rate (ml/hr) | Conversion (%) to 6-APA |
|---|---|
| 10 | 90.6 |
| 15 | 90.2 |
| 30 | 74.2 |
| 60 | 56.1 |
| 72 | 42.2 |
| 110 | 34.4 |

Example 3

1. *Escherichia coli* ATCC 11105 is inoculated into one liter of an aqueous nutrient medium (pH 7.0) containing the same ingredients as described in Example 1 — (1). The medium is cultivated at 30°C for 24 hours under shaking. Then, the medium is centrifuged. The microbial cells thus collected show the penicillin amidase activity of 6.9 units/g. 12 g of the microbial cells are suspended in 48 ml of a physiological saline solution. 9 g of acryloylamide, 480 mg of N,N'-methylene-bis-acryloylamide, 6 ml of 5 % β-(dimethylamino)-propionitrile and 6 ml of 2.5 % potassium persulfate are added to the suspension. Then, the suspension is allowed to stand at 37°C for 30 minutes. The stiff gel obtained is granulated by passing it through a sieve to form particles of 3 mm in diameter. 120 ml of an immobilized preparation of *Escherichia coli* ATCC 11105 are obtained. Penicillin amidase activity: 5 units/ml.

2. 10 g of Penicillin V are suspended in 450 ml of water, and the suspension is adjusted to pH 9.0 with 2N-sodium hydroxide to dissolve Penicillin V therein. Water is added to the resultant aqueous Penicillin V solution to bring its total volume to 500 ml. The, 120 ml of the immobilized preparation of *Escherichia coli* ATCC 11105 are suspended in the aqueous Penicillin V solution. The suspension thus obtained is stirred for 40°C for a certain period of time. The percentage conversion of Penicillin V to 6-APA in the suspension is shown in Table 2.

Table 2

| Reaction time (hr) | Conversion (%) to 6-APA |
|---|---|
| 2 | 12 |
| 4 | 26 |
| 6 | 42 |
| 10 | 89 |
| 24 | 92 |
| 30 | 91 |

After the Penicillin V suspension is stirred for 30 hours as described above, it is filtered to remove insoluble materials. The filtrate thus obtained is treated in the same manner as described in Example 1 — (2). 5.27 g of 6-APA are obtained. M.p. 204° – 207°C (decomp.)

Example 4

1. *Escherichia coli* ATCC 11105 is inoculated into 1 liter of an aqueous nutrient medium (pH 7.0) containing the same ingredients as described in Example 1 — (1). The medium is cultivated at 30°C for 24 hours under shaking. Then, the medium is centrifuged. The microbial cells thus collected show the penicillin amidase activity of 6.9 units/g. 12 g of the microbial cells are suspended in 48 ml of a physiological saline solution. 9 g of acryloylamide, 480 mg of bis(acryloylamidomethyl)ether, 6 ml of 5 % β-(dimethylamino)-propionitrile and 6 ml of 2.5 % ammonium persulfate are added to the suspension. Then, the suspension is allowed to stand at 37°C for 1 hour. The stiff gel obtained is granulated by passing it through a sieve to form particles of 3 mm in diameter. 120 ml of an immobilized preparation of *Escherichia coli* ATCC 11105 are obtained. Penicillin amidase activity: 5 units/ml.

2. 120 ml of the immobilized preparation of *Escherichia coli* ATCC 11105 are charged into a 2.1 cm × 34.8 cm column. An aqueous 2 % Penicillin G solution (pH 9.0) is continuously passed through the column at 40°C at a flow rate as shown in Table 3. The percentage conversion of Penicillin G to 6-APA in the effluent is assayed at 24-hour intervals. The results are shown in Table 3.

Table 3

| Operation time (hr) | Flow rate 30 ml/hr | Flow rate 15 ml/hr |
|---|---|---|
| 24 | 52 | 92 |
| 48 | 51 | 92 |
| 72 | 52 | 90 |
| 96 | 49 | 92 |
| 120 | 50 | 91 |
| 144 | 53 | 89 |
| 168 | 51 | 90 |

Example 5

1. An aqueous nutrient medium (pH 7.0) containing the following ingredients is prepared:

| | | |
|---|---|---|
| Glucose | 3 | w/v % |
| Corn steep liquor | 2.5 | |
| Yeast extract | 0.5 | |
| Sodium chloride | 0.5 | |
| Calcium carbonate | 0.2 | |
| Phenoxyacetic acid | 0.2 | |

*Streptomyces griseus* IFO 3355 is inoculated into one liter of the medium. The medium is cultivated at 30°C for 48 hours. Then, the medium is centrifuged. The microbial cells thus collected show the penicillin amidase activity of 3.6 units/g. 24 g of the microbial cells are suspended in 96 ml of a physiological saline solution. 18 g of acryloylamide, 960 mg of N,N'-methylene-bis-acryloylamide, 12 ml of 5 % β-(dimethylamino)-propionitrile and 12 ml of 2.5 % potassium persulfate are added to the suspension. Then, the suspension is allowed to stand at 37°C for 30 minutes. The stiff gel obtained is granulated by passing it through a sieve to form particles of 3 mm in diameter. 240 ml of an immobilized preparation of *Streptomyces griseus* IFO 3355 are obtained. Penicillin amidase activity: 0.5 units/ml.

2. 240 ml of the immobilized preparation of *Streptomyces griseus* IFO 3355 are added to 500 ml of an aqueous 2 % Penicillin V solution (pH 9.0). The mixture is stirred at 40°C for 30 hours. Then, the reaction mixture is filtered, and the filtrate thus obtained is treated in the same manner as described in Example 1 — (2). 5.11 g of 6-APA are obtained. M.p. 204° – 207°C (decomp.)

Example 6

1. *Nocardia gardneri* ATCC 9604 is inoculated into one liter of an aqueous nutrient medium (pH 7.0) containing the same ingredients as described in Example 5 — (1). The medium is cultivated at 30°C for 72 hours under shaking. Then, the medium is centrifuged. The microbial cells thus collected show the penicillin amidase activity of 3.6 units/g. 24 g of the microbial cells are treated in the same manner as described in Example 5 — (1). 240 ml of an immobilized preparation of *Nocardia gardneri* ATCC 9604 are obtained. Penicillin amidase activity: 0.5 units/ml.

2. 240 ml of the immobilized preparation of *Nocardia gardneri* ATCC 9604 are added to 500 ml of an aqueous 2 % Penicillin G solution (ph 9.0). The mixture is stirred at 40°C for 30 hours. Then, the reaction mixture is filtered, and the filtrate thus obtained is treated in the same manner as described in Example 1 — (2). 5.26 g of 6-APA are obtained. M.p. 204° − 207°C (decomp.)

Example 7

1. 24 g of the microbial cells of *Escherichia coli* ATCC 11105 are suspended in 96 ml of a physiological saline solution. 18 g of acryloylamide, 960 mg of N,N′-di-acryloylethyleneurea, 12 ml of 5 % β-(dimethylamino)-propionitrile and 12 ml of 2.5 % ammonium persulfate are added to the suspension. Then, the suspension is allowed to stand at 37°C for 30 minutes. The stiff gel obtained is granulated by passing it through a sieve to form particles of 3 mm in diameter. 240 ml of an immobilized preparation of *Escherichia coli* ATCC 11105 are obtained. Penicillin amidase activity: 0.5 units/ml.

2. 240 ml of the immobilized preparation of *Escherichia coli* ATCC 11105 are added to 500 ml of an aqueous 2 % Penicillin V solution (pH 9.0). The mixture is stirred at 40°C for 30 hours. Then, the reaction mixture is filtered, and the filtrate thus obtained is treated in the same manner as described in Example 1 — (2). 5.11 g of 6-APA are obtained. M.p. 204° − 207°C (decomp.)

Example 8

1. 24 g of the microbial cells of *Escherichia coli* ATCC 11105 are suspended into 240 ml of a physiological saline solution. 600 mg of bis(acrylamidomethyl) ether, 18 ml of 0.112 % N,N′,N′-tetramethylenediamine and 2 ml of 2.5 % ammonium persulfate are added to the suspension. Then, the suspension is allowed to stand at 37°C for 60 minutes. The stiff gel obtained is granulated by passing it through a sieve to form particles of 3 mm in diameter. 420 ml of the immobilized preparation of *Escherichia coli* ATCC 11105 are obtained. Penicillin amidase activity: 0.3 units/ml.

2. 420 ml of the immobilized preparation of *Escherichia coli* ATCC 11105 are added to 500 ml of an aqueous 2 % Penicillin G solution (pH 9.0). The mixture is stirred at 40°C for 30 hours. Then, the reaction mixture is filtered, and filtrate thus obtained is treated in the same manner as described in Example 1 — (2). 5.26 g of 6-APA are obtained. M.p. 204° − 207°C (decomp.)

Example 9

1. 24 g of the microbial cells of *Escherichia coli* ATCC 11105 are suspended into 240 ml of a physiological saline solution. 600 mg of N,N′-methylene-bis(acrylamide), 18 ml of 0.112 % N,N′,N′-tetramethylenediamine and 2 ml of 2.5 % ammonium persulfate are added to the suspension. Then, the suspension is allowed to stand at 30°c for 60 minutes. The stiff gel obtained is granulated by passing it through a sieve to form particles of 3 mm in diameter. 420 ml of the immobilized preparation of *Escherichia coli* ATCC 11105 are obtained. Penicillin amidase activity: 0.3 units/ml.

2. 420 ml of the immobilized preparation of *Escherichia coli* ATCC 11105 are added to 500 ml of an aqueous 2 % Penicillin G solution (pH 9.0). The mixture is stirred at 40°C for 30 hours. Then, the reaction mixture is filtered, and filtrate thus obtained is treated in the same manner as described in Example 1 — (2). 5.26 g of 6-APA are obtained. M.p. 204° − 207°C (decomp.)

Example 10

1. 24 g of the microbial cells of *Escherichia coli* ATCC 11105 are suspended into 240 ml of a physiological saline solution. 600 mg of N,N′-di-acryloylethyleneurea, 18 ml of 0.112 % N,N′,N′-tetramethylenediamine and 2 ml of 2.5 % potassium persulfate are added to the suspension. Then, the suspension is allowed to stand at 37°C for 30 minutes. The stiff gel obtained is granulated by passing it through a sieve to form particles of 3 mm in diameter. 420 ml of the immobilized preparation of *Escherichia coli* ATCC 11105 are obtained. Penicillin amidase activity: 0.2 units/ml.

2. 420 ml of the immobilized preparation of *Escherichia coli* ATCC 11105 are added to 500 ml of an aqueous 2 % Penicillin V solution (pH 9.0). The mixture is stirred at 40°C for 48 hours. Then, the reaction mixture is filtered, and filtrate thus obtained is treated in the same manner as described in Example 1 — (2). 5.11 g of 6-APA are obtained. M.p. 204° − 207°C (decomp.)

What we claim is:

1. A process for preparing 6-aminopenicillanic acid which comprises the steps of polymerizing at least one acryloly monomer selected from the group consisting of acryloylamide, N,N′-lower alkylene-bis-acryloylamide, bis acryloylamidomethyl ether, and N,N′-diacryloyl-ethyleneurea, in an aqueous suspension of a penicillin amidase-producing microorganism in the presence of a polymerization initiator and a polymerization accelerator to produce an immobilized penicillin amidase-producing microorganism, and subjecting the immobilized penicillin amidase-producing microorganism to enzymatic reaction with penicillin.

2. A process for preparing 6-aminopenicillanic acid which comprises the steps of polymerizing N,N′-lower alkylene-bis-acryloylamide, bis(acryloylamidomethyl)ether of N,N′-diacryloyl-ethyleneurea, or copolymerizing acryloylamide with N,N′-lower alkylene-bis-acryloylamide, bis(acryloylamidomethyl)ether or N,N′-di-acryloyl-ethyleneurea, in an aqueous suspension of a penicillin amidase-producing microorganism in the presence of a polymerization initiator and a polymerization accelerator to produce an immobilized penicillin amidase-producing microorganism, and subjecting the immobilized penicillin amidase-producing microorganism to enzymatic reaction with penicillin.

3. The process accroding to claim 2, wherein the polymerization is carried out at 0° to 50°C, and the enzymatic reaction is carried out at 25° to 50°C at a pH of 7 to 9.5.

4. The process according to claim 2, wherein the polymerization is carried out at 20° to 40°C, and the enzymatic reaction is carried out at 30° to 45°C.

5. The process according to claim 2, wherein the polymerization initiator is selected from the group consisting of potassium persulfate, ammonium persulfate, vitamin $B_2$ and Methylene Blue, and the polymerization accelerator is selected from the group consisting of β-(dimethylamino)-propionitrile and N,N,N',N'-tetramethylethylenediamine.

6. The process according to claim 2, wherein the penicillin amidase-producing microorganism is selected from the group consisting of *Escherichia coli* ATCC 9637, *Escherichia coli* ATCC 11105, *Streptomyces griseus* IFO 3355, *Nocardid gardneri* ATCC 9604, *Micrococcus roseus* IFO 3764, *Pseudomonas aeruginosa* OUT 8252 and *Alkaligenes faecalis* OUT 8025.

7. A process for preparing 6-aminopenicillanic acid which comprises the steps of polymerizing N,N'-lower alkylene-bis-acryloylamide, bis(acryloylamidomethyl)ether or N,N'-diacryloyl-ethyleneurea in an aqueous suspension containing 0.32 to 3.2 g, per g of the acryloyl monomer, of a penicillin amidase-producing microorganism in the presence of a polymerization initiator and a polymerization accelerator at 0° to 50°C, passing the resultant immobilized penicillin amidase-producing microorganism through a sieve to form granules (2.5 to 5.5 mm in diameter) of the immobilized penicillin amidase-producing microorganism, and then subjecting said granules of the immobilized microorganism to enzymatic reaction with penicillin at 25°C to 50°C at a pH of 7 to 9.5.

8. The process according to claim 7, wherein the polymerization initiator is selected from the group consisting of potassium persulfate, ammonium persulfate, vitamin $B_2$ and Methylene Blue, and the polymerization accelerator is selected from the group consisting of β-(dimethylamino)-propionitrile and N,N,N', N'-tetramethyl-ethylenediamine.

9. A process for preparing 6-aminopenicillanic acid which comprises the steps of copolymerizing acryloylamide with 5 to 160 mg, per g of acryloylamide, of N,N'-lower alkylene-bis-acryloylamide, bis(acryloylamidomethyl)ether or N,N'-acryloyl-ethyleneurea in an aqueous suspension containing 0.32 to 3.2 g, per g of the acryloyl monomers, of a penicillin amidase-producing microorganism in the presence of a polymerization initiator and a polymerization accelerator at 0° to 50°C, passing the resultant immobilized penicillin amidase-producing microorganism through a sieve to form granules (2.5 to 5.5 mm in diameter) of the immobilized penicillin amidase-producing microorganism, and then subjecting said granules of the immobilized microorganism to enzymatic reaction with penicillin at 25° to 50°C at a pH of 7 to 9.5.

10. The process according to claim 9, wherein the polymerization initiator is selected from the group consisting of potassium persulfate, ammonium persulfate, vitamin $B_2$ and Methylene Blue and the polymerization accelerator is selected from the group consisting of β-(dimethylamino)-propionitrile and N,N,N',N'-tetramethyl-ethylenediamine.

11. An immobilized penicillin amidase-producing microorganism comprising a penicillin amidase-producing microorganism tightly entrapped into the lattice of a semi-permeable acryloyl polymer selected from the group consisting of homopolymer of N,N'-lower alkylene-bis-acryloylamide, bis(acryloylamidomethyl)ether or N,N'-acryloyl-ethylene-urea, copolymer of acryloylamide, and N,N'-lower alkylene-bis-acryloylamide, copolymer of acryloylamide and bis-(acryloylamidomethyl)ether and copolymer of acryloylamide and N,N'-acryloyl-ethyleneurea.

12. The immobilized penicillin amidase-producing microorganism as claimed in claim 11, wherein 0.32 to 3.2 g, per g of the acryloyl polymer, of the penicillin amidase-producing microorganism is entrapped.

13. The immobilized penicillin amidase-producing microorganism as claimed in claim 12, wherein said semipermeable acryloyl polymer is granules of 2.5 to 5.5 mm in diameter.

14. The immobilized penicillin amidase-producing microorganism as claimed in claim 12, wherein 0.32 to 3.2 g, per g of the acryloyl polymer, of the penicillin amidase-producing microorganism is entrapped in a copolymer of acryloylamide and 5 to 1.60 m, per g of acryloylamide, of N,N'-lower alkylene-bis-acryloylamide, bis(acryloylamidomethyl) ether or N,N'-acryloyl-ethyleneurea.

* * * * *